United States Patent [19]

Wozney et al.

[11] Patent Number: 5,187,076

[45] Date of Patent: * Feb. 16, 1993

[54] DNA SEQUENCES ENCODING BMP-6 PROTEINS

[75] Inventors: John M. Wozney, Hudson; Elizabeth A. Wang, Carlisle; Vicki A. Rosen, Brookline; Anthony J. Celeste, Hudson, all of Mass.

[73] Assignee: Genetics Institute, Inc., Cambridge, Mass.

[ * ] Notice: The portion of the term of this patent subsequent to Apr. 21, 2009 has been disclaimed.

[21] Appl. No.: 490,033

[22] Filed: Mar. 7, 1990

Related U.S. Application Data

[63] Continuation-in-part of Ser. No. 370,544, Jun. 23, 1989, which is a continuation-in-part of Ser. No. 347,559, May 4, 1989, abandoned, which is a continuation-in-part of Ser. No. 329,610, Mar. 28, 1989, abandoned, which is a continuation-in-part of Ser. No. 179,100, Apr. 8, 1988, Pat. No. 5,013,649, and a continuation-in-part of Ser. No. 179,101, Apr. 8, 1988, abandoned, and a continuation-in-part of Ser. No. 179,197, Apr. 8, 1988, which is a continuation-in-part of Ser. No. 28,285, Mar. 20, 1987, abandoned, and a continuation-in-part of Ser. No. 31,346, Mar. 26, 1987, Pat. No. 4,877,864, which is a continuation-in-part of Ser. No. 943,332, Dec. 17, 1986, abandoned, and a continuation-in-part of Ser. No. 880,776, Jul. 1, 1986, abandoned.

[51] Int. Cl.[5] .................... C12P 21/02; C12P 19/34; C12N 15/00; C12N 1/00; C12N 5/00; C12N 1/21; C12N 1/18; C07K 3/00; C07H 15/12

[52] U.S. Cl. .................... 435/69.1; 435/91; 435/172.3; 435/235.1; 435/320.1; 435/252.3; 435/240.1; 435/255; 435/256; 536/23.5; 536/23.51; 530/350; 535/18; 535/22; 535/34; 535/38; 535/55; 535/62; 535/70; 535/72

[58] Field of Search .................... 435/69.1, 91, 172.1, 435/235, 240.1, 262.3, 320.1, 172.3, 255, 256; 536/27; 510/350; 535/18, 22, 24, 38, 55, 62, 70, 72

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,256 | 6/1984 | Urist | 424/423 |
| 4,563,350 | 1/1986 | Nathan | 424/95 |
| 4,608,199 | 8/1986 | Caplan et al. | 530/414 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1986 | Seyedin | 530/353 |
| 4,789,732 | 12/1988 | Urist | 530/350 |
| 4,795,804 | 1/1989 | Urist et al. | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck | 435/69.4 |
| 4,968,590 | 11/1990 | Kuberasampath et al. | 530/326 |
| 5,011,691 | 4/1991 | Oppermann | 424/423 |

FOREIGN PATENT DOCUMENTS

| | | |
|---|---|---|
| 2017466 | 12/1990 | Canada . |
| 336760 | 6/1989 | European Pat. Off. . |
| 0409472 | 1/1991 | European Pat. Off. . |
| 0416578 | 3/1991 | European Pat. Off. . |
| WO89/09787 | 10/1989 | World Int. Prop. O. . |
| WO89/09788 | 10/1989 | World Int. Prop. O. . |
| WO90/03733 | 4/1990 | World Int. Prop. O. . |
| WO91/02744 | 3/1991 | World Int. Prop. O. . |
| WO91/05802 | 5/1991 | World Int. Prop. O. . |

OTHER PUBLICATIONS

Wozney et al, Science vol. 242, pp. 1528-1534 (1988).
Maniatis et al, Molecular Cloning, a Laboratory Manual Cold Spring Habor Laboratory CSH, N.Y. (1982) pp. 310-323 & 404-433.
Lyons, et al., *Proc. Natl. Acad. Sci (USA)*, 86:4554-4558 (Jun. 1989).
Urist, et al., *Science*, 220: 680-686 (1983).
Luyten, et al., *The Journal of Biological Chemistry*, 264(23): 13377-13380 (Aug. 15, 1989).
Sampath, et al., *Proc. Natl. Acad. Sci.*, 84: 7109-7113 (1987).

*Primary Examiner*—Joan Ellis
*Attorney, Agent, or Firm*—Ellen J. Kapinos; Bruce M. Eisen

[57] ABSTRACT

Purified BMP-6 proteins and processes for producing them are disclosed. The proteins may be used in the treatment of bone and/or cartilage defects and in wound healing and related tissue repair.

27 Claims, 8 Drawing Sheets

FIGURE 1

1 TCTAGAGGTGAGAGCAGCCAACAAGAGAAAAAATCAAAACCGCAATAAATCCGGCTCTCAT 61
  LeuGluValArgAlaAlaAsnLysArgLysAsnGlnAsnArgAsnLys<u>SerGlySerHis</u>
     (1)                                              (15)

62 CAGGACTCCTCTAGAATGTCCAGTGTTGGAGATTATAACACCAGTGAACAAAAACAAGCC 121
   <u>GlnAspSerSerArg</u>MetSerSerValGlyAspTyrAsnThrSerGluGlnLysGlnAla
      (23)

122 TGTAAAAAGCATGAACTCTATGTGAGTTTCCGGGATCTGGGATGGCAGGACTGGATTATA 181
    CysLysLys<u>HisGluLeuTyrValSerPhe</u>ArgAspLeuGlyTrpGlnAspTrpIleIle
             (42)

182 GCACCAGAAGGATATGCTGCATTTTATTGTGATGGAGAATGTTCTTTTCCACTCAATGCC 241
    AlaProGluGlyTyrAlaAlaPheTyrCysAspGlyGluCysSerPheProLeuAsnAla

242 CATATGAATGCCACCAATCATGCCATAGTTCAGACTCTGGTTCACCTGATGTTTCCTGAC 301
    HisMetAsnAlaThrAsnHisAlaIleValGlnThrLeuValHisLeuMetPheProAsp

302 CACGTACCAAAGCCTTGCTGCGCGACAAACAAACTAAATGCCATCTCTGTGTTGTACTTT 361
    HisValProLysProCysCysAlaThrAsnLysLeuAsnAlaIleSerValLeuTyrPhe

362 GATGACAGCTCCAATGTCATTTTGAAAAAGTACAGAAATATGGTCGTGCGTTCGTGTGGT 421
    AspAspSerSerAsnValIleLeuLysLysTyrArgAsnMetValValArgSerCysGly

422 TGCCACTAATAGTGCATAATAATGGTAATAAGAAAAAGATCTGTATGGAGGTTTATGA 481
    CysHisEnd
      (140)

481 CTACAATAAAAAATATCTTTCGGATAAAAGGGGAATTTAATAAAATTAGTCTGGCTCATT 540

541 TCATCTCTGTAACCTATGTACAAGAGCATGTATATAGT 578

FIGURE 2

```
              9               18              27              36              45
CTG CTG GGC ACG CGT GCT GTG TGG GCC TCA GAG GCG GGC TGG CTG
Leu Leu Gly Thr Arg Ala Val Trp Ala Ser Glu Ala Gly Trp Leu
(1)
              54              63              72              81              90
GAG TTT GAC ATC ACG GCC ACC AGC AAC CTG TGG GTC CTG ACT CCG
Glu Phe Asp Ile Thr Ala Thr Ser Asn Leu Trp Val Leu Thr Pro 99             108             117             126             135
CAG CAC AAC ATG GGG CTG CAG CTG AGC GTG GTC ACG CGT GAT GGG
Gln His Asn MET Gly Leu Gln Leu Ser Val Val Thr Arg Asp Gly 144             153             162             171             180
CTC AGC ATC AGC CCT GGG GCC GCG GGC CTG GTG GGC AGG GAC GGC
Leu Ser Ile Ser Pro Gly Ala Ala Gly Leu Val Gly Arg Asp Gly 189             198             207             216             225
CCC TAC GAC AAG CAG CCC TTC ATG GTG GCC TTC TTC AAG GCC AGT
Pro Tyr Asp Lys Gln Pro Phe MET Val Ala Phe Phe Lys Ala Ser 234             243             252             261             270
GAG GTC CAC GTG CGC AGT GCC CGG TCG GCC CCC GGG CGG CGC CGG
Glu Val His Val Arg Ser Ala Arg Ser Ala Pro Gly Arg Arg Arg 279             288             297             306             315
CAG CAG GCC CGG AAC CGC TCC ACC CCG GCC CAG GAC GTG TCG CGG
Gln Gln Ala Arg Asn Arg Ser Thr Pro Ala Gln Asp Val Ser Arg
                             (97)
             324             333             342             351             360
GCC TCC AGC GCC TCA GAC TAC AAC AGC AGC GAG CTG AAG ACG GCC
Ala Ser Ser Ala Ser Asp Tyr Asn Ser Ser Glu Leu Lys Thr Ala 369             378             387             396             405
TGC CGG AAG CAT GAG CTC TAC GTG AGC TTC CAG GAC CTG GGG TGG
Cys Arg Lys His Glu Leu Tyr Val Ser Phe Gln Asp Leu Gly Trp
(121)       (124)
             414             423             432             441             450
CAG GAC TGG ATC ATT GCC CCC AAG GGC TAC GCT GCC AAC TAC TGT
Gln Asp Trp Ile Ile Ala Pro Lys Gly Tyr Ala Ala Asn Tyr Cys 459             468             477             486             495
GAC GGA GAA TGT TCG TTC CCT CTC AAC GCA CAC ATG AAC GCT ACC
Asp Gly Glu Cys Ser Phe Pro Leu Asn Ala His MET Asn Ala Thr 504             513             522             531             540
AAC CAT GCC ATC GTG CAG ACC CTG GTT CAC CTC ATG AAC CCC GAG
Asn His Ala Ile Val Gln Thr Leu Val His Leu MET Asn Pro Glu
```

FIGURE 2
(con't)

```
         549            558            567            576            585
TAC GTC CCC AAA CCG TGC TGC GCG CCC ACG AAA CTG AAC GCC ATC
Tyr Val Pro Lys Pro Cys Cys Ala Pro Thr Lys Leu Asn Ala Ile 594            603            612            621            630
TCG GTG CTC TAC TTC GAC GAC AAC TCC AAT GTC ATC CTG AAG AAG
Tyr Phe Asp Asp Asn Ser Asn Val Ile Leu Lys Lys Tyr Arg Asn 639            648            647            666            676
TAC CGG AAC ATG GTC GTA CGA GCG TGT GGG TGC CAC TGACTCGGGG
Tyr Arg Asn MET Val Val Arg Ala Cys Gly Cys His 686            696            706            716            726
TGAGTGGCTG    GGGACGCTGT    GCACACACTG    CCTGGACTCC    TGGATCACGT 736            746            756            766            776
CCGCCTTAAG    CCCACAGAGG    CCCCCGGGAC    ACAGGAGGAG    ACCCCGAGGC 786            796            806            816            826
CACCTTCGGC    TGGCGTTGGC    CTTTCCGCCC    AACGCAGACC    CGAAGGGACC 836            846            856            866            876
CTGTCCGCCC    CTTGCTCACA    CCGTGAGCGT    TGTGAGTAGC    CATCGGGCTC

886
TAGGAAGCAG    CACTCGAG
```

FIGURE 3A

```
          10         20         30         40         50
    CGACCATGAG AGATAAGGAC TGAGGGCCAG GAAGGGGAAG CGAGCCCGCC 60         70         80         90        100
    GAGAGGTGGC GGGGACTGCT CACGCCAAGG GCCACAGCGG CCGCGCTCCG 110        120        130        140        150
    GCCTCGCTCC GCCGCTCCAC GCCTCGCGGG ATCCGCGGGG GCAGCCCGGC 159        168        177        186        195
    CGGGCGGGG ATG CCG GGG CTG GGG CGG AGG GCG CAG TGG CTG TGC
               MET Pro Gly Leu Gly Arg Arg Ala Gln Trp Leu Cys
               (1)

204        213        222        231        240
    TGG TGG TGG GGG CTG CTG TGC AGC TGC TGC GGG CCC CCG CCG CTG
    Trp Trp Trp Gly Leu Leu Cys Ser Cys Cys Gly Pro Pro Pro Leu 249        258        267        276        285
    CGG CCG CCC TTG CCC GCT GCC GCG GCC GCC GCC GCC GGG GGG CAG
    Arg Pro Pro Leu Pro Ala Ala Ala Ala Ala Ala Ala Gly Gly Gln 294        303        312        321        330
    CTG CTG GGG GAC GGC GGG AGC CCC GGC CGC ACG GAG CAG CCG CCG
    Leu Leu Gly Asp Gly Gly Ser Pro Gly Arg Thr Glu Gln Pro Pro 339        348        357        366        375
    CCG TCG CCG CAG TCC TCC TCG GGC TTC CTG TAC CGG CGG CTC AAG
    Pro Ser Pro Gln Ser Ser Ser Gly Phe Leu Tyr Arg Arg Leu Lys 384        393        402        411        420
    ACG CAG GAG AAG CGG GAG ATG CAG AAG GAG ATC TTG TCG GTG CTG
    Thr Gln Glu Lys Arg Glu MET Gln Lys Glu Ile Leu Ser Val Leu 429        438        447        456        465
    GGG CTC CCG CAC CGG CCC CGG CCC CTG CAC GGC CTC CAA CAG CCG
    Gly Leu Pro His Arg Pro Arg Pro Leu His Gly Leu Gln Gln Pro 474        483        492        501        510
    CAG CCC CCG GCG CTC CGG CAG CAG GAG GAG CAG CAG CAG CAG CAG
    Gln Pro Pro Ala Leu Arg Gln Gln Glu Glu Gln Gln Gln Gln Gln 519        528        537        546        555
    CAG CTG CCT CGC GGA GAG CCC CCT CCC GGG CGA CTG AAG TCC GCG
    Gln Leu Pro Arg Gly Glu Pro Pro Pro Gly Arg Leu Lys Ser Ala 564        573        582        591        600
    CCC CTC TTC ATG CTG GAT CTG TAC AAC GCC CTG TCC GCC GAC AAC
    Pro Leu Phe MET Leu Asp Leu Tyr Asn Ala Leu Ser Ala Asp Asn
```

FIGURE 3B

```
        609             618             627             636             645
GAC GAG GAC GGG GCG TCG GAG GGG GAG AGG CAG CAG TCC TGG CCC
Asp Glu Asp Gly Ala Ser Glu Gly Glu Arg Gln Gln Ser Trp Pro 654             663             672             681             690
CAC GAA GCA GCC AGC TCG TCC CAG CGT CGG CAG CCG CCC CCG GGC
His Glu Ala Ala Ser Ser Ser Gln Arg Arg Gln Pro Pro Pro Gly Ser 699             708             717             726             735
GCC GCG CAC CCG CTC AAC CGC AAG AGC CTT CTG GCC CCC GGA TCT
Pro Pro Gly Ala Ala His Pro Leu Asn Arg Lys Ser Leu Leu Ala 744             753             762             771             780
GGC AGC GGC GGC GCG TCC CCA CTG ACC AGC GCG CAG GAC AGC GCC
Gly Ser Gly Gly Ala Ser Pro Leu Thr Ser Ala Gln Asp Ser Ala 789             798             807             816             825
TTC CTC AAC GAC GCG GAC ATG GTC ATG AGC TTT GTG AAC CTG GTG
Phe Leu Asn Asp Ala Asp MET Val MET Ser Phe Val Asn Leu Val 834             843             852             861             870
GAG TAC GAC AAG GAG TTC TCC CCT CGT CAG CGA CAC CAC AAA GAG
Glu Tyr Asp Lys Glu Phe Ser Pro Arg Gln Arg His His Lys Glu 879             888             897             906             915
TTC AAG TTC AAC TTA TCC CAG ATT CCT GAG GGT GAG GTG GTG ACG
Phe Lys Phe Asn Leu Ser Gln Ile Pro Glu Gly Glu Val Val Thr 924             933             942             951             960
GCT GCA GAA TTC CGC ATC TAC AAG GAC TGT GTT ATG GGG AGT TTT
Phe Arg Ile Tyr Lys Asp Cys Val MET Ala Ala Glu Gly Ser Phe 969             978             987             996             1005
AAA AAC CAA ACT TTT CTT ATC AGC ATT TAT CAA GTC TTA CAG GAG
Lys Asn Gln Thr Phe Leu Ile Ser Ile Tyr Gln Val Leu Gln Glu 1014            1023            1032            1041            1050
CAT CAG CAC AGA GAC TCT GAC CTG TTT TTG TTG GAC ACC CGT GTA
His Gln His Arg Asp Ser Asp Leu Phe Leu Leu Asp Thr Arg Val 1059            1068            1077            1086            1095
GTA TGG GCC TCA GAA GAA GGC TGG CTG GAA TTT GAC ATC ACG GCC
Val Trp Ala Ser Glu Glu Gly Trp Leu Glu Phe Asp Ile Thr Ala 1104            1113            1122            1131            1140
ACT AGC AAT CTG TGG GTT GTG ACT CCA CAG CAT AAC ATG GGG CTT
Thr Ser Asn Leu Trp Val Val Thr Pro Gln His Asn MET Gly Leu
```

FIGURE 3C

```
            1149              1158              1167              1176              1185
      CAG CTG AGC       GTG GTG ACA       AGG GAT GGA       GTC CAC GTC       CAC CCC CGA
      Gln Leu Ser       Val Val Thr       Arg Asp Gly       Val His Val       His Pro Arg 1194              1203              1212              1221              1230
      GCC GCA GGC       CTG GTG GGC       AGA GAC GGC       CCT TAC GAT       AAG CAG CCC
      Ala Ala Gly       Leu Val Gly       Arg Asp Gly       Pro Tyr Asp       Lys Gln Pro 1239              1248              1257              1266              1275
      TTC ATG GTG       GCT TTC TTC       AAA GTG AGT       GAG GTC CAC       GTG CGC ACC
      Phe MET Val       Ala Phe Phe       Lys Val Ser       Glu Val His       Val Arg Thr 1284              1293              1302              1311              1320
      ACC AGG TCA       GCC TCC AGC       CGG CGC CGA       CAA CAG AGT       CGT AAT CGC
      Thr Arg Ser       Ala Ser Ser       Arg Arg Arg       Gln Gln Ser       Arg Asn Arg
                                                            (382)
            1329              1338              1347              1356              1365
      TCT ACC CAG       TCC CAG GAC       GTG GCG CGG       GTC TCC AGT       GCT TCA GAT
      Ser Thr Gln       Ser Gln Asp       Val Ala Arg       Val Ser Ser       Ala Ser Asp
      (388)
            1374              1383              1392              1401              1410
      TAC AAC AGC       AGT GAA TTG       AAA ACA GCC       TGC AGG AAG       CAT GAG CTG
      Tyr Asn Ser       Ser Glu Leu       Lys Thr Ala       Cys Arg Lys       His Glu Leu
                                                            (412)
            1419              1428              1437              1446              1455
      TAT GTG AGT       TTC CAA GAC       CTG GGA TGG       CAG GAC TGG       ATC ATT GCA
      Tyr Val Ser       Phe Gln Asp       Leu Gly Trp       Gln Asp Trp       Ile Ile Ala 1464              1473              1482              1491              1500
      CCC AAG GGC       TAT GCT GCC       AAT TAC TGT       GAT GGA GAA       TGC TCC TTC
      Pro Lys Gly       Tyr Ala Ala       Asn Tyr Cys       Asp Gly Glu       Cys Ser Phe 1509              1518              1527              1536              1545
      CCA CTC AAC       GCA CAC ATG       AAT GCA ACC       AAC CAC GCG       ATT GTG CAG
      Pro Leu Asn       Ala His MET       Asn Ala Thr       Asn His Ala       Ile Val Gln 1554              1563              1572              1581              1590
      ACC TTG GTT       CAC CTT ATG       AAC CCC GAG       TAT GTC CCC       AAA CCG TGC
      Thr Leu Val       His Leu MET       Asn Pro Glu       Tyr Val Pro       Lys Pro Cys 1599              1608              1617              1626              1635
      TGT GCG CCA       ACT AAG CTA       AAT GCC ATC       TCG GTT CTT       TAC TTT GAT
      Cys Ala Pro       Thr Lys Leu       Asn Ala Ile       Ser Val Leu       Tyr Phe Asp 1644              1653              1662              1671              1680
      GAC AAC TCC       AAT GTC ATT       CTG AAA AAA       TAC AGG AAT       ATG GTT GTA
      Asp Asn Ser       Asn Val Ile       Leu Lys Lys       Tyr Arg Asn       MET Val Val
```

FIGURE 3D

```
      1689        1698        1708        1718        1728
AGA GCT TGT GGA TGC CAC TAACTCGAAA CCAGATGCTG GGGACACACA
Arg Ala Cys Gly Cys His
                    (513)
      1738        1748        1758        1768        1778
TTCTGCCTTG GATTCCTAGA TTACATCTGC CTTAAAAAAA CACGGAAGCA 1788        1798        1808        1818        1828
CAGTTGGAGG TGGGACGATG AGACTTTGAA ACTATCTCAT GCCAGTGCCT 1838        1848        1858        1868        1878
TATTACCCAG GAAGATTTTA AAGGACCTCA TTAATAATTT GCTCACTTGG 1888        1898        1908        1918        1928
TAAATGACGT GAGTAGTTGT TGGTCTGTAG CAAGCTGAGT TTGGATGTCT 1938        1948        1958        1968        1978
GTAGCATAAG GTCTGGTAAC TGCAGAAACA TAACCGTGAA GCTCTTCCTA 1988        1998        2008        2018        2028
CCCTCCTCCC CCAAAAACCC ACCAAAATTA GTTTTAGCTG TAGATCAAGC 2038        2048        2058        2068        2078
TATTTGGGGT GTTTGTTAGT AAATAGGGAA AATAATCTCA AAGGAGTTAA 2088        2098        2108        2118        2128
ATGTATTCTT GGCTAAAGGA TCAGCTGGTT CAGTACTGTC TATCAAAGGT 2138        2148        2158        2168        2178
AGATTTTACA GAGAACAGAA ATCGGGGAAG TGGGGGGAAC GCCTCTGTTC 2188        2198        2208        2218        2228
AGTTCATTCC CAGAAGTCCA CAGGACGCAC AGCCCAGGCC ACAGCCAGGG 2238        2248        2258        2268        2278
CTCCACGGGG CGCCCTTGTC TCAGTCATTG CTGTTGTATG TTCGTGCTGG 2288        2298        2308        2318        2328
AGTTTTGTTG GTGTGAAAAT ACACTTATTT CAGCCAAAAC ATACCATTTC 2338        2348        2358        2368        2378
TACACCTCAA TCCTCCATTT GCTGTACTCT TTGCTAGTAC CAAAAGTAGA 2388        2398        2408        2418        2428
CTGATTACAC TGAGGTGAGG CTACAAGGGG TGTGTAACCG TGTAACACGT 2438        2448        2458        2468        2478
GAAGGCAGTG CTCACCTCTT CTTTACCAGA ACGGTTCTTT GACCAGCACA
```

FIGURE 3E

```
         2488       2498       2508       2518       2528
     TTAACTTCTG GACTGCCGGC TCTAGTACCT TTTCAGTAAA GTGGTTCTCT 2538       2548       2558       2568       2578
     GCCTTTTTAC TATACAGCAT ACCACGCCAC AGGGTTAGAA CCAACGAAGA 2588       2598       2608       2618       2628
     AAATAAAATG AGGGTGCCCA GCTTATAAGA ATGGTGTTAG GGGGATGAGC 2638       2648       2658       2668       2678
     ATGCTGTTTA TGAACGGAAA TCATGATTTC CCTGTAGAAA GTGAGGCTCA 2688       2698       2708       2718       2728
     GATTAAATTT TAGAATATTT TCTAAATGTC TTTTTCACAA TCATGTGACT 2738       2748       2758       2768       2778
     GGGAAGGCAA TTTCATACTA AACTGATTAA ATAATACATT TATAATCTAC 2788       2798       2808       2818       2828
     AACTGTTTGC ACTTACAGCT TTTTTTGTAA ATATAAACTA TAATTTATTG 2838       2848       2858       2868       2878
     TCTATTTTAT ATCTGTTTTG CTGTGGCGTT GGGGGGGGGG CCGGGCTTTT 2888       2898       2908       2918
     GGGGGGGGGG GTTTGTTTGG GGGGTGTCGT GGTGTGGGCG GGCGG
```

DNA SEQUENCES ENCODING BMP-6 PROTEINS

CROSS REFERENCE TO RELATED APPLICATIONS

This application is a continuation-in-part of U.S. Ser. No. 370,544 filed Jun. 23, 1989, which is a continuation-in-part of U.S. Ser. No. 347,559 filed May 4, 1989, now abandoned, which is a continuation-in-part of U.S. Ser. No. 329,610 filed Mar. 28, 1989, now abandoned, which is a continuation-in-part of U.S. Ser. Nos. 179,100 now U.S. Pat. No. 5,013,649; 179,101 (now abandoned); and 179,197 filed Apr. 8, 1988, which are continuations-in-part of U.S. Ser. Nos. 028,285 filed Mar. 20, 1987, now abandoned and 031,346 filed Mar. 26, 1987, now U.S. Pat. No. 4,877,864 which are continuations-in-part of U.S. Ser. Nos. 943,332 filed Dec. 17, 1986, now abandoned and 880,776 filed Jul. 1, 1986, now abandoned.

The present invention relates to a family of purified proteins, termed BMP-6 proteins (wherein BMP is bone morphogenic protein), which exhibit the ability to induce cartilage and/or bone formation and processes for obtaining them. These proteins may be used to induce bone and/or cartilage formation and in wound healing and tissue repair.

The invention provides purified human BMP-6 proteins, substantially free from other proteins with which they are co-produced. The BMP-6 proteins of the invention are characterized by an amino acid sequence comprising acid #412 to amino acid #513 set forth in Table III. The amino acid sequence from amino acid #412 to #513 is encoded by the DNA sequence of Table III from nucleotide #1393 to nucleotide #1698. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of stimulating promoting, or otherwise inducing cartilage and/or bone formation.

The invention further provides bovine BMP-6 proteins characterized by the amino acid sequence comprising amino acid #121 to amino acid #222 set forth in Table II. The amino acid sequence from #121 to #222 is encoded by the DNA sequence of Table II from nucleotide #361 to #666 of Table II. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of inducing cartilage and/or bone formation.

Human BMP-6 proteins of the invention are produced by culturing a cell transformed with a DNA sequence comprising nucleotide #1393 to nucleotide #1698 as shown in Table III or a substantially similar sequence, recovering and purifying from the culture medium a protein comprising amino acid #412 to amino acid #513 or a substantially similar sequence.

Bovine proteins of the invention may be produced by culturing a cell transformed with a DNA comprising nucleotide #361 through nucleotide #666 as set forth in Table II or a substantially similar sequence and recovering and purifying from the culture medium a protein comprising amino acid #121 to amino acid #222 as set forth in Table II.

The invention further provides a method wherein the proteins described above are utilized for obtaining related human protein/s or other mammalian cartilage and/or bone formation protein/s. Such methods are known to those skilled in the art of genetic engineering. One method for obtaining such proteins involves utilizing the human BMP-6 coding sequence or a portion thereof from nucleotide #160–#1698 to design probes for screening human genomic and/or cDNA libraries to isolate human genomic and/or cDNA sequences. Additional methods within the art may employ the bovine and human BMP-6 proteins of the invention to obtain other mammalian BMP-6 cartilage and/or bone formation proteins. Having identified the nucleotide sequences, the proteins are produced by culturing a cell transformed with the nucleotide sequence. This sequence or portions thereof hybridizes under stringent conditions to the nucleotide sequence substantially as shown in Table II comprising nucleotide #1 to nucleotide #666 or the nucleotide sequence or portions thereof substantially as shown in Table III comprising nucleotide #160 to #1698 and encodes a protein exhibiting cartilage and/or bone formation activity. The expressed protein is recovered and purified from the culture medium. The purified BMP-6 proteins of the invention are substantially free from other proteinaceous materials with which they are coproduced, as well as from other contaminants.

The BMP-6 proteins of the invention are further characterized by the ability to promote, stimulate or otherwise induce the formation of cartilage and/or bone. It is further contemplated that the ability of these proteins to induce the formation of cartilage and/or bone is exhibited by the ability to demonstrate cartilage and/or bone formation activity in the rat bone formation assay described below. It is further contemplated that the proteins of the invention demonstrate activity in this rat bone formation assay at a concentration of 10 μg–500 μg/gram of bone formed. More particularly, it is contemplated these proteins may be characterized by the ability of 1 μg of the protein to score at least +2 in the rat bone formation assay described below using either the original or modified scoring method.

Another aspect of the invention provides pharmaceutical compositions containing a therapeutically effective amount of a protein of the invention in a pharmaceutically acceptable vehicle or carrier. These compositions of the invention may be used to induce bone and/ or cartilage formation. These compositions may also be used for wound healing and tissue repair. Further compositions of the invention may include, in addition to a BMP-6 protein, at least one other therapeutically useful agent such as the proteins designated BMP-1, BMP-2A and -2B, BMP-3, BMP-5, and BMP-7 disclosed respectively in co-owned U.S. patent applications Ser. No. 179,101, Ser. No. 179,100, and Ser. No. 179,197, Ser. No. 437,409, Ser. No. 438,919. Other therapeutically useful agents include growth factors such as epidermal growth factor (EGF), fibroblast growth factor (FGF), transforming growth factors (TGF-α and TGF-β) and platelet derived growth factor (PDGF). The compositions of the invention may also include an appropriate matrix, for instance, for delivery and support of the composition and/or providing a surface for bone and-/or cartilage growth.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a BMP-6 protein of the invention in a pharmaceutically acceptable vehicle or carrier including a martrix. These methods may also entail the administration of a BMP-6 protein in conjunction with at least one of the "BMP" proteins disclosed in the co-owned applications described above. In addition, these methods may also include the administration of a protein of the invention with other growth factors including EGF, FGF, TGF-α, TGF-β, and PDFG.

Still a further aspect of the invention are DNA sequences coding for expression of a protein of the invention. Such sequences include the sequence of nucleotides in a 5' to 3' direction illustrated in Table II or Table III or DNA sequences which hybridize under stringent conditions with the DNA sequence of Table II or Table III and encode a protein demonstrating ability to induce cartilage and/or bone formation. Such ability to induce cartilage and/or bone formation may be demonstrated in the rat bone formation assay described below. It is contemplated that these proteins demonstrate activity in this assay at a concentration of 10 μg 500 μg/gram of bone formed. More particularly, it is contemplated that these proteins demonstrate the ability of 1 μg of the protein to score at least +2 in the rat bone formation assay using either the original or modified scoring method. Allelic or variations as described herein below of the sequences of Table II and III, whether such nucleotide changes result in changes in the peptide sequence or not, are also included in the present invention.

A further aspect of the invention provides vectors containing a DNA sequence as described above in operative association with an expression control sequence therefor. These vectors may be employed in a novel process for producing a protein of the invention in which a cell line transformed with a DNA sequence directing expression of a protein of the invention in operative association with an expression control sequence therefor, is cultured in a suitable culture medium and a protein of the invention is isolated and purified therefrom. This claimed process may employ a number of known cells, both prokaryotic and eukaryotic, as host cells for expression of the polypeptide.

Other aspects and advantages of the present invention will be apparent upon consideration of the following detailed description and preferred embodiments thereof.

DETAILED DESCRIPTION OF THE INVENTION

The purified human BMP-6 proteins of the invention are characterized by an amino acid sequence comprising amino acid #412 to #513 as set forth in Table III. In one embodiment a BMP-6 protein of the invention comprises amino acid #388 to #513 of Table III. In a further embodiment the BMP-6 protein comprises amino acid #382 to #513 of Table III.

The purified BMP-6 human cartilage/bone proteins of the present invention may be produced by culturing a host cell transformed with a DNA sequence comprising nucleotide #1393 to nucleotide #1698 as set forth in Table III or substantially homologous sequences operatively linked to a heterologous regulatory control sequence and recovering, isolating and purifying from the culture medium a protein comprising amino acid #412 to amino acid #513 as set forth in Table III or a substantially homologous sequence.

In another embodiment, purified human BMP-6 proteins may be produced by culturing a host cell transformed with a DNA sequence comprising nucleotide #1321 to #1698 as set forth in Table III or substantially homologous sequences operatively linked to a heterologous regulatory control sequence and recovering and purifying from the culture medium a protein comprising amino acid #388 to #513 asset forth in Table III or a substantially homologous sequence.

In another embodiment, purified human BMP-6 proteins may be produced by culturing a host cell transformed with a DNA sequence comprising nucleotide #1303 to #1698 as set forth in Table III or substantially homologous sequences operatively linked to a heterologous regulatory control sequence and recovering and purifying from the culture medium a protein comprising amino acid #382 to #513 as set forth in Table III or a substantially homologous sequence.

The purified human BMP-6 proteins are substantially free from other proteinaceous materials with which they are coproduced, as well as from other contaminants.

Purified BMP-6 bovine cartilage/bone protein of the present invention are produced by culturing a host cell transformed with a DNA sequence comprising nucleotide #361 to nucleotide #666 as set forth in Table II or substantially homologous sequences and recovering from the culture medium a protein comprising amino acid #121 to amino acid #222 as set forth in Table II or a substantially homologous sequence. In another embodiment the bovine protein is produced by culturing a host cell transformed with a sequence comprising nucleotide #289 to #666 of Table II and recovering and purifying a protein comprising amino acid #97 to amino acid #222. The purified BMP-6 bovine proteins are substantially free from other proteinaceous materials with which they are co-produced, as well as from other contaminants.

These proteins of the invention may be further characterized by the ability to demonstrate cartilage and/or bone formation activity. This activity may be demonstrated, for example, in the rat bone formation assay as described in Example III. It is further contemplated that these proteins demonstrate activity in the assay at a concentration of 10 μg –500 μg/gram of bone formed. The proteins may be further characterized by the ability of 1 μg to score at least +2 in this assay.

BMP-6 proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE, the protein electrophoreses with a molecular weight of approximately 14,000–20,000 daltons.

The proteins provided herein also include factors encoded by the sequences similar to those of Table II and Table III but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of Table II or Table III are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein may involve modifications of a glycosylation site. These modifications may involve O-linked or N-linked glycosylation sites. For instance, the absence of glycosylation or only partial glycosylation at the asparagine-linked glycosylation sites results from amino acid substitution or deletion at the asparagine-linked glycosylation recognition sites present in the sequences of the proteins of the invention, for example, as shown in Table II or Table III. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

The present invention also encompasses the novel DNA sequences, free of association with DNA sequences encoding other proteinaceous materials, and coding on expression for the proteins of the invention. These DNA sequences include those depicted in Tables II and III in a 5' to 3' direction or portions thereof. Further included are those sequences which hybridize under stringent hybridization conditions [see, T. Maniatis et al, *Molecular Cloning (A Laboratory Manual)*, Cold Spring Harbor Laboratory (1982), pages 387 to 389]to the DNA sequence of Table II or Table III and demonstrate cartilage and/or bone formation activity. Such cartilage and/or bone formation activity may be in the rat bone formation assay. An example of one such stringent hybridization condition is hybridization at 4 × SSC at 65° C., followed by a washing in 0.1 × SCC at 65° C. for an hour. Alternatively, an exemplary stringent hybridization condition is in 50% formamide, 4 × SCC at 42° C.

Similarly, DNA sequences which encode proteins similar to the protein encoded by the sequence of Table II or Table III, but which differ in codon sequence due to the degeneracies of the genetic code or allelic variations (naturally-occurring base changes in the species population which may or may not result in an amino acid change) also encode the proteins of the invention described herein. Variations in the DNA sequences of Table II and Table III which are caused by point mutations or by induced modifications (including insertion, deletion, and substitution) to enhance the activity, half-life or production of the polypeptides encoded thereby are also encompassed in the invention.

In a further aspect, the invention provides a method for obtaining related human proteins or other mammalian BMP-6 proteins. One method for obtaining such proteins entails, for instance, utilizing the human BMP-6 coding sequence disclosed herein to probe a human genomic library using standard techniques for the human gene or fragments thereof. Sequences thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity. This activity may be demonstrated in the rat bone formation assay of Example III.

Another aspect of the present invention provides a novel method for producing the proteins of the invention. This method involves culturing a suitable cell line, which has been transformed with a DNA sequence coding for expression of a protein of the invention, under the control of known regulatory sequences. Regulatory sequences include promoter fragments, terminator fragments and other suitable sequences which direct the expression of the protein in an appropriate host cell. Methods for culturing suitable cell lines are within the skill of the art. The transformed cells are cultured and the BMP-6 proteins expressed thereby are recovered and purified from the culture medium using purification techniques known to those skilled in the art. The purified BMP-6 proteins are substantially free from other proteinaceous materials with which they are co-produced, as well as other contaminants. Purified BMP-6 proteins of the invention are substantially free from materials with which the proteins of the invention exist in nature.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines are the monkey COS-1 cell line and the CV-1 cell line.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277-298 (Plenum Press 1986) and references cited therein.

Another aspect of the present invention provides vectors for use in the method of expression of the proteins of the invention. Preferably the vectors contain the full novel DNA sequences described above which code for the novel BMP-6 proteins of the invention. Additionally the vectors also contain appropriate expression control sequences permitting expression of the protein sequences. Alternatively, vectors incorporating modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention. Host cells transformed with such vectors and progeny thereof for use in producing BMP-6 proteins are also provided by the invention.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

A further aspect of the invention is a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the BMP-6 proteins of the invention in admixture with a pharmaceutically acceptable vehicle, carrier or matrix.

It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins, BMP-1, BMP-2 (BMP-2A, BMP-2 Class I), BMP-3, BMP-4 (BMP-2B, BMP-2 Class II), BMP-5 and BMP-7, disclosed in co-owned and co-pending U.S. applications described above. Such methods and compositions of the invention may comprise proteins of the invention or portions thereof in combination with the above-mentioned "BMP" proteins or portions thereof. Such combination may comprise individual separate molecules from each of the proteins or heteromolecules such as heterodimers formed by portions of the respective proteins. For example, a method and composition of the invention may comprise a BMP-6 protein of the invention or a portion thereof linked with a portion of a different "BMP" protein to form a heteromolecule.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-$\alpha$ and TGF-$\beta$), k-fibroblast growth factor (kFGF), parathyroid hormone (PTH), leukemia inhibitory factor (LIF/HILDA/DIA), and insulin-like growth factors (IGF-I and IGF-II). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone proteins. Domestic animals and thoroughbred horses in addition to humans are desired patients for such treatment with the proteins of the present invention The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition includes a matrix capable of delivering the cartilage/bone proteins of the invention to the site of bone and/or cartilage damage, providing a structure for the developing bone and cartilage and optimally capable of being resorbed into the body. Matrices may provide slow release of the cartilage and/or bone inductive proteins proper presentation and appropriate enviroment for cellular infiltration. Matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions are biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-α, TGF-β, and IGF-I to the final composition, may also effect the dosage.

Progress can be monitored by periodic assessment of cartilage and/or bone growth and/or repair. The progress can be monitored, for example, using x-rays, histomorphometric determinations and tetracycline labeling.

The following examples illustrate practice of the present invention in recovering and characterizing bovine cartilage and/or bone proteins of the invention and employing these proteins to recover the corresponding human protein or proteins and in expressing the proteins via recombinant techniques.

EXAMPLE I

Isolation of Bovine Cartilage/Bone Inductive Protein

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4½ C over a 48 hour period with vigorous stirring. The resulting suspension is extracted for 16 hours at 4½ C with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthoo. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath - Reddi assay (described in Example III below) desorbed from the column by 50mM NaAc, 0.25 mM NaCl, 6M urea (pH 4.6). The protein from this step elution is concentrated 20- to 40fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and-/or cartilage formation activity is eluted with 100 mM $KPO_4$ (pH7.4) and 6M urea.

The protein is concentrated approximately 10 times, and solid NaCl added to a final concentration of 0.15M. This material is applied to a heparin - Sepharose column equilibrated in 50 mM $KPO_4$, 150 mM NaCl, 6M urea (pH7.4). After extensive washing of the column with starting buffer, a protein with bone and/or cartilage inductive activity is eluted by 50 mM $KPO_4$, 700mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity corresponds to an approximate 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active bone and/or cartilage formation fractions are pooled. The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Fractions were assayed for cartilage and/or bone formation activity. The active material is further fractionated on a MonoQ column. The protein is dialyzed against 6M urea, 25 mM diethanolamine, pH 8.6 and then applied to a 0.5 by 5 cm MonoQ column (Pharmacia) which is developed with a gradient of 6M urea, 25 mM diethanolamine, pH 8.6 and 0.5 M NaCl, 6M urea, 25 mM diethanolamine, pH 8.6. Fractions are brought to pH3.0 with 10% trifluoroacetic acid (TFA).

Aliquots of the appropriate fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilage/Bone Inductive Factor

A. Molecular Weight

Approximately 5 μg protein from Example I in 6M urea, 25 mM diethanolamine, pH 8.6, approximately 0.3M NaCl is made 0.1% with respect to SDS and dialyzed against 50 mM tris/HCl 0.1% SDS pH 7.5 for 16 hrs. The dialyzed material is then electrophorectically concentrated against a dialysis membrane [Hunkapillar et al *Meth. Enzymol.* 91: 227–236 (1983)]with a small amount of I 125 labelled counterpart. This material (volume approximately 100 μl) is loaded onto a 12% polyacrylamide gel and subjected to SDS-PAGE [Laemmli, U.K. *Nature*, 227:680-685 (1970)]without reducing the sample with dithiothreitol. The molecular weight is determined relative to prestained molecular weight standards (Bethesda Research Labs). Following autoradiography of the unfixed gel the approximate 28,000-30,000 dalton band is excised and the protein electrophoretically eluted from the gel (Hunkapillar et Based on similar purified bone fractions as described in the co-pending "BMP" applications described above wherein bone and/or cartilage activity is found in the 28,000-30,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000-20,000 dalton region having a doublet appearance located by autoradiography of the unfixed gel. A faint band remains at the 28,000-30,000 region. Thus the 28,000-30,000 dalton protein yields a broad region of 14,000-20,000 which may otherwise also be interpreted and described as comprising two broad bands of approximately 14,000-16,000 and 16,000-20,000 daltons.

EXAMPLE III

Rosen Modified Sampath-Reddi Assay

A modified version of the rat bone formation assay described in Sampath and Reddi, *Proc. Natl. Acad. Sci. U.S.A.*, 80:6591-6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1 % TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21-49 day old male Long Evans rats. The implants are removed after 5-21 days. Half of each implant is used for alkaline phosphatase analysis [See, A. H. Reddi et al., *Proc. Natl Acad Sci.*, 69:1601 (1972)].

The other half of each implant is fixed and processed for histological analysis. Glycolmethacrylate sections (1 μm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. Two scoring methods are herein described. The first describes the original scoring method while the second describes the later adopted scoring method. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. The scoring method later adopted (which herein after maybe referred to as the "modified" scoring method) is as follows: Three non-adjacent sections are evaluated from each implant and averaged. "+/—" indicates tentative identification of cartilage or bone; "+2", >25%; "+3+", >50%; "+4", >75%; "+5", >80%. The scores of the individual implants are tabulated to indicate assay variability.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV

Bovine BMP-6 Protein Composition

The gel slice of the approximate 14,000-20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 μg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). One tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the above-identified tryptic fragment and synthesized on an automated DNA synthesizer.

PROBE #1: GTRCTYGANATRCANTC

PROBE #2: GTRCTYGANATRCANAG

PROBE #3: GTRCTYAAYATRCANTC

PROBE #4: GTRCTYAAYATRCANAG

The standard nucleotide symbols in the above identified probes are as follows: A,adenine; C,cytosine;

G,guanine; T,thymine; N, adenosine or cytosine or guanine or thymine; R,adenosine or guanine; and Y,-cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic fragment. These probes are radioactively labeled and employed to screen a bovine cDNA library as described below.

Poly(A) containing RNA is isolated by oligo(dT) cellulose chromatography from total RNA isolated from fetal bovine bone cells by the method of Gehron-Robey et al in *Current Advances in Skeletogenesis*, Elsevier Science Publishers (1985). The total RNA was obtained from Dr. Marian Young, National Institute of Dental Research, National Institutes of Health. A cDNA library is made in lambda gt10 (Toole et al supra) and plated on 50 plates at 8000 recombinants per plate. These recombinants (400,000) are screened on duplicate nitrocellulose filters with a combination of Probes 1, 2, 3, and 4 using the Tetramethylammonium chloride (TMAC) hybridization procedure [see Wozney et al *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plaque purified, a phage plate stock made, and bacteriophage DNA isolated. This DNA is digested with EcoRI and subcloned into M13 and pSP65. The DNA sequence and derived amino acid sequence of this fragment is shown in Table I.

DNA sequence analysis of this fragment in M13 indicates that it encodes the desired tryptic peptide sequence set forth above, and this derived amino acid sequence is preceded by a basic residue (Lys) as predicted by the specificity of trypsin. The underlined portion of the sequence in Table I from amino acid #42 to #48 corresponds to the tryptic fragment identified above from which the oligonucleotide probes are designed. The derived amino acid sequence Ser-Gly-Ser-His-Gln-Asp-Ser-Ser-Arg as set forth in Table I from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending applications mentioned above. This fragment set forth in Table I is a portion of the DNA sequence which encodes a bovine BMP-5 protein. The DNA sequence indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of a bovine BMP-5 cartilage/bone protein.

TABLE I

| | | |
|---|---|---|
| 1 | TCTAGAGGTGAGAGCAGCCAACAAGAGAAAAAATCAAAACCGCAATAAATCCGGCTCTCAT<br>LeuGluValArgAlaAlaAsnLysArgLysAsnGlnAsnArgAsnLys<u>SerGlySerHis</u><br>(1)                                           (15) | 61 |
| 62 | CAGGACTCCTCTAGAATGTCCAGTGTTGGAGATTATAACACCAGTGAACAAAAACAAGCC<br><u>GlnAspSerSerArg</u>MetSerSerValGlyAspTyrAsnThrSerGluGlnLysGlnAla<br>(23) | 121 |
| 122 | TGTAAAAAGCATGAACTCTATGTGAGTTTCCGGGATCTGGGATGGCAGGACTGGATTATA<br>CysLysLys<u>HisGluLeuTyrValSerPheArg</u>AspLeuGlyTrpGlnAspTrpIleIle<br>(42) | 181 |
| 182 | GCACCAGAAGGATATGCTGCATTTTATTGTGATGGAGAATGTTCTTTTCCACTCAATGCC<br>AlaProGluGlyTyrAlaAlaPheTyrCysAspGlyGluCysSerPheProLeuAsnAla | 241 |
| 242 | CATATGAATGCCACCAATCATGCCATAGTTCAGACTCTGGTTCACCTGATGTTTCCTGAC<br>HisMetAsnAlaThrAsnHisAlaIleValGlnThrLeuValHisLeuMetPheProAsp | 301 |
| 302 | CACGTACCAAAGCCTTGCTGCGCGACAAACAAACTAAATGCCATCTCTGTGTTGTACTTT<br>HisValProLysProCysCysAlaThrAsnLysLeuAsnAlaIleSerValLeuTyrPhe | 361 |
| 362 | GATGACAGCTCCAATGTCATTTTGAAAAAGTACAGAAATATGGTCGTGCGTTCGTGTGGT<br>AspAspSerSerAsnValIleLeuLysLysTyrArgAsnMetValValArgSerCysGly | 421 |
| 422 | TGCCACTAATAGTGCATAATAATGGTAATAAGAAAAAAGATCTGTATGGAGGTTTATGA<br>CysHisEnd<br>(140) | 481 |
| 481 | CTACAATAAAAAATATCTTTCGGATAAAAGGGGAATTTAATAAAATTAGTCTGGCTCATT | 540 |
| 541 | TCATCTCTGTAACCTATGTACAAGAGCATGTATATAGT 578 | |

The remaining positive clones isolated with probes #1, #2, #3, and #4 described above are screened with HEL5 and a further clone is identified under reduced stringency conditions [5× SSC, 0.1% SDS, 5× Denhardt's, 100 μg/ml salmon sperm DNA standard hybridization buffer (SHB) at 65° C., wash in 2× SSC 0.1% SDS at 65° C.]. This clone is plaque purified, a phage plate stock made and bacteriophage DNA isolated. The DNA sequence and derived amino acid sequence of a portion of this clone is shown in Table II. This sequence represents the DNA sequence encoding a BMP-6 cartilage/bone protein of the invention.

The first underlined portion of the sequence in Table II from amino acid #97 - amino acid #105 Ser-Thr-Pro-Ala-Gln-Asp-Val-Ser-Arg corresponds to the tryptic fragment found in the 28,000-30,000 dalton purified bovine bone preparation (and its reduced form at approximately 18,000-20,000 dalton reduced form) as described in the "BMP" co-pending applications mentioned above. The second underlined sequence in Table II from amino acid #124–amino acid #130 corresponds to the tryptic fragment identified above from which the oligonucleotide probes are designed.

The DNA sequence of Table II indicates an open reading frame of 666 base pairs starting from the 5' end of the sequence of Table II, encoding a partial peptide of 222 amino acid residues. An in-frame stop codon (TGA) indicates that this clone encodes the carboxyterminal part of a bovine BMP-6 protein of the invention. Based on knowledge of other BMP proteins and other proteins in the TGF-$\beta$ family, it is predicted that the precursor polypeptide would be cleaved at the three basic residues (ArgArgArg) to yield a mature peptide beginning with residue 90 or 91 of the sequence of Table II.

TABLE II

```
            9              18             27             36             45             54
CTG CTG GGC ACG CGT GCT GTG TGG GCC TCA GAG GCG GGC TGG CTG GAG TTT GAC
Leu Leu Gly Thr Arg Ala Val Trp Ala Ser Glu Ala Gly Trp Leu Glu Phe Asp
(1)

63             72             81             90             99            108
ATC ACG GCC ACC AGC AAC CTG TGG GTC CTG ACT CCG CAG CAC AAC ATG GGG CTG
Ile Thr Ala Thr Ser Asn Leu Trp Val Leu Thr Pro Gln His Asn MET Gly Leu 117            126            135            144            153            162
CAG CTG AGC GTC GTC ACG CGT GAT GGG CTC AGC ATC AGC CCT GGG GCC GCG GGC
Gln Leu Ser Val Val Thr Arg Asp Gly Leu Ser Ile Ser Pro Gly Ala Ala Gly 171            180            189            198            207            216
CTG GTG GGC AGG GAC GGC CCC TAC GAC AAG CAG CCC TTC ATG GTG GCC TTC TTC
Leu Val Gly Arg Asp Gly Pro Tyr Asp Lys Gln Pro Phe MET Val Ala Phe Phe 225            234            243            252            261            270
AAG GCC AGT GAG GTC CAC GTG CGC AGT GCC CGG TCG GCC CCC GGG CGG CGC CGG
Lys Ala Ser Glu Val His Val Arg Ser Ala Arg Ser Ala Pro Gly Arg Arg Arg 279            288            297            306            315            324
CAG CAG GCC CGG AAC CGC TCC ACC CCG GCC CAG GAC GTG TCG CGG GCC TCC AGC
Gln Gln Ala Arg Asn Arg Ser Thr Pro Ala Gln Asp Val Ser Arg Ala Ser Ser
                             (97)

333            342            351            360            369            378
GCC TCA GAC TAC AAC AGC AGC GAG CTG AAG ACG GCC TGC CGG AAG CAT GAG CTC
Ala Ser Asp Tyr Asn Ser Ser Glu Leu Lys Thr Ala Cys Arg Lys His Glu Leu
                                                        (121)       (124)

387            396            405            414            423            432
TAC GTG AGC TTC CAG GAC CTG GGG TGG CAG GAC TGG ATC ATT GCC CCC AAG GGC
Tyr Val Ser Phe Gln Asp Leu Gly Trp Gln Asp Trp Ile Ile Ala Pro Lys Gly 441            450            459            468            477            486
TAC GCT GCC AAC TAC TGT GAC GGA GAA TGT TCG TTC CCT CTC AAC GCA CAC ATG
Tyr Ala Ala Asn Tyr Cys Asp Gly Glu Cys Ser Phe Pro Leu Asn Ala His MET 495            504            513            522            531            540
AAC GCT ACC AAC CAT GCC ATC GTG CAG ACC CTG GTT CAC CTC ATG AAC CCC GAG
Asn Ala Thr Asn His Ala Ile Val Gln Thr Leu Val His Leu MET Asn Pro Glu 549            558            567            576            585            594
TAC GTC CCC AAA CCG TGC TGC GCG CCC ACG AAA CTG AAC GCC ATC TCG GTG CTC
Tyr Val Pro Lys Pro Cys Cys Ala Pro Thr Lys Leu Asn Ala Ile Ser Val Leu 603            612            621            630            639            648
TAC TTC GAC GAC AAC TCC AAT GTC ATC CTG AAG AAG TAC CGG AAC ATG GTC GTA
Tyr Phe Asp Asp Asn Ser Asn Val Ile Leu Lys Lys Tyr Arg Asn MET Val Val 657            666            676       .    686            696            706            716
CGA GCG TGT GGG TGC CAC TGACTCGGGG TGAGTGGCTG GGACGCTGT GCACACACTG CCTGGACTCC
Arg Ala Cys Gly Cys His
                (222)

726            736            746            756            766            776            786
TGGATCACGT CCGCCTTAAG CCCACAGAGG CCCCCGGGAC ACAGGAGGAG ACCCCGAGGC CACCTTCGGC 796            806            816            826            836            846            856
TGGCGTTGGC CTTTCCGCCC AACGCAGACC CGAAGGGACC CTGTCCGCCC CTTGCTCACA CCGTGAGCGT
```

TABLE II-continued

```
       866            876           886
TGTGAGTAGC CATCGGGCTC TAGGAAGCAG CACTCGAG
```

EXAMPLE V
Human BMP-6 Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single standed M13 $^{32}$P-labeled probe corresponding to the above mentioned BMP-5 EcoRI-BglII fragment containing nucleotides 1–465 of the sequence of Table I. A strongly hybridizing band is detected in the lane corresponding to the human osteosarcoma cell line U-20S RNA. Another nitrocellulose replica is hybridized to a single stranded M13 $^{32}$P-labeled probe containing the PstI-SmaI fragment of bovine BMP-6 (corresponding to nucleotides 106–261 of Table II). It is found that several RNA species in the lane corresponding to U-20S RNA hybridize to this probe.

A cDNA Library is made in the vector lambda ZAP (Stratagene) from U-20S poly(A)-containing RNA using established techniques (Toole et al.). 750,000 recombinants of this library are plated and duplicate nitrocellulose replicas made. The SmaI fragment of bovine BMP-6 corresponding to nucleotides 259–751 of Table II is labeled by nick-translation and hybridized to both sets of filters in SHB at 65°. One set of filters is washed under stringent conditions (0.2× SSC, 0.1% SDS at 65°), the other under reduced stringency conditions (1× SSC, 0.1% SDS at 65°). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106–378 of Table II), and the third to the nick-translated BMP-5 XbaI fragment (nucleotides 1–76 of Table I). Hybridization and washes are carried out under stringent conditions.

Six clones which hybridize to the second probe more strongly than to the third are picked and transformed into plasmids. Restriction mapping, Southern blot analysis, and DNA sequence analysis of these plasmids indicate that there are two classes of clones. Clones U2-7 and U2-10 contain human BMP-6 coding sequence based on their stronger hybridization to the second probe and closer DNA homology to the bovine BMP-6 sequence of Table II than the other 4 clones. DNA sequence data derived from these clones indicates that they encode a partial polypeptide of 132 amino acids comprising the carboxy-terminus of the human BMP-6 protein. U2-7 was deposited with the American Type Culture Collection (ATCC), Rockville, Md. on Jun. 23, 1989 under accession number 68021.

A primer extended cDNA library is made from U-2 OS mRNA using the oligonucleotide GGAATC-CAAGGCAGAATGTG, the sequence being based on the 3' untranslated sequence of the human BMP-6 derived from the clone U2-10. This library is screened with an oligonucleotide of the sequence CAGAGTC-GTAATCGC, derived from the BMP-6 coding sequence of U2-7 and U2-10. Hybridization is in standard hybridization buffer (SHB) at 42 degrees centigrade, with wash conditions of 42 degrees centigrade, 5× SSC, 0.1% SDS. Positively hybridizing clones are isolated. The DNA insert of one of these clones, PEH6-2, indicates that it extends further in a 5' direction than either U2-7 or U2-10. A primer extended cDNA library constructed from U-20S mRNA as above is screened with an oligonucleotide of the sequence GCCTCTCCCCCTCCGACGCCCCGTCCTCGT, derived from the sequence near the 5' end of PEH6-2. Hybridization is at 65 degrees centigrade in SHB, with washing at 65 degrees centigrade in 2× SSC, 0.1% SDS. Positively hybridizing recombinants are isolated and analyzed by restriction mapping and DNA sequence analysis.

The 5' sequence of the insert of one of the positively hybridizing recombinants, PE5834 #7, is used to design an oligonucleotide of the sequence CTGCTGCTCCTCCTGCTGCCGGAGCGC. A random primed cDNA library [synthesized as for an oligo (dT) primed library except that (dN)$_6$ is used as the primer] is screened with this oligonucleotide by hybridization at 65 degrees centigrade in SHB with washing at 65 degrees centigrade in 1× SSC, 0.1% SDS. A positively hybridizing clone, RP10, is identified, isolated, and the DNA sequence sequence from the 5' end of its insert is determined. This sequence is used to design an oligonucletide of the sequence TCGGGCTTCCTGTACCGGCGGCTCAAGACG-CAGGAGAAGCGGGAGATGCA. A human placenta cDNA library (Stratagene catalog #936203) is screened with this oligonucleotide by hybridization in SHB at 65 degrees centigrade, and washing at 65 degrees centigrade with 0.2× SSC, 0.1% SDS. A positively hybridizing recombinant designated BMP6C35 is isolated. DNA sequence analysis of the insert of this recombinant indicates that it encodes the complete human BMP-6 protein. BMP6C35 was deposited with the American Type Culture Collection, 12301 Parklawn Drive, Rockville, Md. USA on Mar. 1, 1990 under Accession Number 68245.

The DNA and derived amino acid sequence of the majority of the insert of BMP6C35 is given in Table III. This DNA sequence contains an open reading frame of 1539 base pairs which encodes the 513 amino acid human BMP-6 protein precursor. The presumed initiator methionine codon is L preceded by a 5'untranslated sequence of 159 base pairs with stop codons in all three reading frames. The stop codon at nucleotides 1699–1701 is followed by at least 1222 base pairs of 3'untranslated sequence. It is noted that U2-7 has a C residue at the position corresponding to the T residue at position 1221 of BMP6C35; U2-7 also has a C residue at the position corresponding to the G residue at position 1253 of BMP6C35. These do not cause amino acid differences in the encoded proteins, and presumably represent allelic variations.

The oligonucleotide TCGGGCTTCCTGTACCGGCGGCTCAAGACG-

CAGGAGAAGCGGGAGATGCA is used to screen a human genomic library (Toole et al supra), by hybridizing nitrocellulose replicas of 1×10⁶ recombinants with the oligonucleotide in SHB at 65 degrees centigrade, and washing at 65 degrees centigrade with 0.2× SSC, 0.1% SDS. Positively hybridizing clones are purified. The oligonucleotide hybridizing region is localized to an approximately 1.5 kb Pst I fragment. DNA sequence analysis of this fragment confirms the 5' sequence indicated in Table III.

The DNA sequence of the human BMP-6 clone set forth in Table III reveals an open reading frame of 1539 bp encoding a protein of 513 amino acids. The first underlined portion of the sequence in Table III from amino acid #388 to #396, Ser-Thr-Gln-Ser-Gln-Asp-Val-Ala-Arg, corresponds to the similar sequence Ser-Thr-Pro-Ala-Gln-Asp-Val-Ser-Arg of the bovine sequence described above and set forth in Table II. The second underlined sequence in Table III from amino acid #415 through #421 His-Glu-Leu-Tyr-Val-Ser-Phe, corresponds to the tryptic fragment identified above from which the oligonucleotide probes are designed. When the tryptic sequence His-Glu-Leu-Tyr-Val-Ser-Phe-(Ser) described above was identified, it was noted to be similar to a sequence found in other BMP proteins for example the sequence His-Pro-Leu-Tyr-Val-Asp-Phe-Ser found in the bovine and human cartilage/bone protein BMP-2A sequence as described in co-pending U.S. application Ser. No. 179,100. BMP-6 therefore represents a new member of the BMP subfamily of TGF-β like molecules which includes the molecules BMP-2 (also sometimes referred to as BMP-2A or BMP-2 Class I), 3, 4 (also sometimes referred to as BMP-2B or BMP-2 Class II), 5 and 7 described in co-pending applications cited above.

Based on knowledge of other BMP proteins, as well as other proteins in the TGF-β family, BMP-6 is predicted to be synthesized as a precursor molecule and the precursor polypeptide would be cleaved between amino acid #381 and amino acid #382 yielding a 132 amino acid mature polypeptide with a calculated molecular weight of approximately 15 Kd. The mature form of BMP-6 contains three potential N-linked glycosylation sites per polypeptide chain.

It is contemplated that the active BMP-6 protein molecule is a dimer. It is further contemplated tht the processing of BMP-6 into the mature form involves dimerization and removal of the N-terminal region in a manner 15 analogous to the processing of the related protein TGF-β [L.E. Gentry, et al., *Molec. & Cell. Biol.* 8:4162 (1988); R. Dernyck, et al., *Nature* 316:701 (1985)].

TABLE III

```
          10         20         30         40         50
CGACCATGAG AGATAAGGAC TGAGGGCCAG GAAGGGGAAG CGAGCCCGCC 60         70         80         90        100
GAGAGGTGGC GGGGACTGCT CACGCCAAGG GCCACAGCGG CCGCGCTCCG 110        120        130        140        150
GCCTCGCTCC GCCGCTCCAC GCCTCGCGGG ATCCGCGGGG GCAGCCCGGC 159        168        177        186        195
CGGGCGGGG  ATG CCG GGG CTG GGG CGG AGG GCG CAG TGG CTG TGC
           MET Pro Gly Leu Gly Arg Arg Ala Gln Trp Leu Cys
           (1)

204        213        222        231        240
TGG TGG TGG GGG CTG CTG TGC AGC TGC TGC GGG CCC CCG CCG CTG
Trp Trp Trp Gly Leu Leu Cys Ser Cys Cys Gly Pro Pro Pro Leu 249        258        267        276        285
CGG CCG CCC TTG CCC GCT GCC GCG GCC GCC GCC GCC GGG GGG CAG
Arg Pro Pro Leu Pro Ala Ala Ala Ala Ala Ala Ala Gly Gly Gln 294        303        312        321        330
CTG CTG GGG GAC GGC GGG AGC CCC GGC CGC ACG GAG CAG CCG CCG
Leu Leu Gly Asp Gly Gly Ser Pro Gly Arg Thr Glu Gln Pro Pro 339        348        357        366        375
CCG TCG CCG CAG TCC TCC TCG GGC TTC CTG TAC CGG CGG CTC AAG
Pro Ser Pro Gln Ser Ser Ser Gly Phe Leu Tyr Arg Arg Leu Lys 384        393        402        411        420
ACG CAG GAG AAG CGG GAG ATG CAG AAG GAG ATC TTG TCG GTG CTG
Thr Gln Glu Lys Arg Glu MET Gln Lys Glu Ile Leu Ser Val Leu 429        438        447        456        465
GGG CTC CCG CAC CGG CCC CGG CCC CTG CAC GGC CTC CAA CAG CCG
Gly Leu Pro His Arg Pro Arg Pro Leu His Gly Leu Gln Gln Pro 474        483        492        501        510
CAG CCC CCG GCG CTC CGG CAG CAG GAG GAG CAG CAG CAG CAG CAG
Gln Pro Pro Ala Leu Arg Gln Gln Glu Glu Gln Gln Gln Gln Gln
```

TABLE III-continued

```
          519             528             537             546             555
CAG  CTG  CCT  CGC  GGA  GAG  CCC  CCT  CCC  GGG  CGA  CTG  AAG  TCC  GCG
Gln  Leu  Pro  Arg  Gly  Glu  Pro  Pro  Pro  Gly  Arg  Leu  Lys  Ser  Ala 564             573             582             591             600
CCC  CTC  TTC  ATG  CTG  GAT  CTG  TAC  AAC  GCC  CTG  TCC  GCC  GAC  AAC
Pro  Leu  Phe  MET  Leu  Asp  Leu  Tyr  Asn  Ala  Leu  Ser  Ala  Asp  Asn 609             618             627             636             645
GAC  GAG  GAC  GGG  GCG  TCG  GAG  GGG  GAG  AGG  CAG  CAG  TCC  TGG  CCC
Asp  Glu  Asp  Gly  Ala  Ser  Glu  Gly  Glu  Arg  Gln  Gln  Ser  Trp  Pro 654             663             672             681             690
CAC  GAA  GCA  GCC  AGC  TCG  TCC  CAG  CGT  CGG  CAG  CCG  CCC  CCG  GGC
His  Glu  Ala  Ala  Ser  Ser  Ser  Gln  Arg  Arg  Gln  Pro  Pro  Pro  Gly 699             708             717             726             735
GCC  GCG  CAC  CCG  CTC  AAC  CGC  AAG  AGC  CTT  CTG  GCC  CCC  GGA  TCT
Pro  Pro  Gly  Ala  Ala  His  Pro  Leu  Asn  Arg  Lys  Ser  Leu  Leu  Ala 744             753             762             771             780
GGC  AGC  GGC  GGC  GCG  TCC  CCA  CTG  ACC  AGC  GCG  CAG  GAC  AGC  GCC
Gly  Ser  Gly  Gly  Ala  Ser  Pro  Leu  Thr  Ser  Ala  Gln  Asp  Ser  Ala 789             798             807             816             825
TTC  CTC  AAC  GAC  GCG  GAC  ATG  GTC  ATG  AGC  TTT  GTG  AAC  CTG  GTG
Phe  Leu  Asn  Asp  Ala  Asp  MET  Val  MET  Ser. Phe  Val  Asn  Leu  Val 834             843             852             861             870
GAG  TAC  GAC  AAG  GAG  TTC  TCC  CCT  CGT  CAG  CGA  CAC  CAC  AAA  GAG
Glu  Tyr  Asp  Lys  Glu  Phe  Ser  Pro  Arg  Gln  Arg  His  His  Lys  Glu 879             888             897             906             915
TTC  AAG  TTC  AAC  TTA  TCC  CAG  ATT  CCT  GAG  GGT  GAG  GTG  GTG  ACG
Phe  Lys  Phe  Asn  Leu  Ser  Gln  Ile  Pro  Glu  Gly  Glu  Val  Val  Thr 924             933             942             951             960
GCT  GCA  GAA  TTC  CGC  ATC  TAC  AAG  GAC  TGT  GTT  ATG  GGG  AGT  TTT
Phe  Arg  Ile  Tyr  Lys  Asp  Cys  Val  MET  Ala  Ala  Glu  Gly  Ser  Phe 969             978             987             996            1005
AAA  AAC  CAA  ACT  TTT  CTT  ATC  AGC  ATT  TAT  CAA  GTC  TTA  CAG  GAG
Lys  Asn  Gln  Thr  Phe  Leu  Ile  Ser  Ile  Tyr  Gln  Val  Leu  Gln  Glu 1014            1023            1032            1041            1050
CAT  CAG  CAC  AGA  GAC  TCT  GAC  CTG  TTT  TTG  TTG  GAC  ACC  CGT  GTA
His  Gln  His  Arg  Asp  Ser  Asp  Leu  Phe  Leu  Leu  Asp  Thr  Arg  Val 1059            1068            1077            1086            1095
GTA  TGG  GCC  TCA  GAA  GAA  GGC  TGG  CTG  GAA  TTT  GAC  ATC  ACG  GCC
Val  Trp  Ala  Ser  Glu  Glu  Gly  Trp  Leu  Glu  Phe  Asp  Ile  Thr  Ala 1104            1113            1122            1131            1140
ACT  AGC  AAT  CTG  TGG  GTT  GTG  ACT  CCA  CAG  CAT  AAC  ATG  GGG  CTT
Thr  Ser  Asn  Leu  Trp  Val  Val  Thr  Pro  Gln  His  Asn  MET  Gly  Leu 1149            1158            1167            1176            1185
CAG  CTG  AGC  GTG  GTG  ACA  AGG  GAT  GGA  GTC  CAC  GTC  CAC  CCC  CGA
Gln  Leu  Ser  Val  Val  Thr  Arg  Asp  Gly  Val  His  Val  His  Pro  Arg 1194            1203            1212            1221            1230
GCC  GCA  GGC  CTG  GTG  GGC  AGA  GAC  GGC  CCT  TAC  GAT  AAG  CAG  CCC
Ala  Ala  Gly  Leu  Val  Gly  Arg  Asp  Gly  Pro  Tyr  Asp  Lys  Gln  Pro 1239            1248            1257            1266            1275
TTC  ATG  GTG  GCT  TTC  TTC  AAA  GTG  AGT  GAG  GTC  CAC  GTG  CGC  ACC
Phe  MET  Val  Ala  Phe  Phe  Lys  Val  Ser  Glu  Val  His  Val  Arg  Thr 1284            1293            1302            1311            1320
ACC  AGG  TCA  GCC  TCC  AGC  CGG  CGC  CGA  CAA  CAG  AGT  CGT  AAT  CGC
Thr  Arg  Ser  Ala  Ser  Ser  Arg  Arg  Arg  Gln  Gln  Ser  Arg  Asn  Arg
                                 (382)
```

TABLE III-continued

```
         1329            1338            1347            1356            1365
TCT ACC CAG TCC CAG GAC GTG GCG CGG GTC TCC AGT GCT TCA GAT
Ser Thr Gln Ser Gln Asp Val Ala Arg Val Ser Ser Ala Ser Asp
(388)

1374            1383            1392            1401            1410
TAC AAC AGC AGT GAA TTG AAA ACA GCC TGC AGG AAG CAT GAG CTG
Tyr Asn Ser Ser Glu Leu Lys Thr Ala Cys Arg Lys His Glu Leu
                                               (412)

1419            1428            1437            1446            1455
TAT GTG AGT TTC CAA GAC CTG GGA TGG CAG GAC TGG ATC ATC ATT GCA
Tyr Val Ser Phe Gln Asp Leu Gly Trp Gln Asp Trp Ile Ile Ile Ala 1464            1473            1482            1491            1500
CCC AAG GGC TAT GCT GCC AAT TAC TGT GAT GGA GAA TGC TCC TTC
Pro Lys Gly Tyr Ala Ala Asn Tyr Cys Asp Gly Glu Cys Ser Phe 1509            1518            1527            1536            1545
CCA CTC AAC GCA CAC ATG AAT GCA ACC AAC CAC GCG ATT GTG CAG
Pro Leu Asn Ala His MET Asn Ala Thr Asn His Ala Ile Val Gln 1554            1563            1572            1581            1590
ACC TTG GTT CAC CTT ATG AAC CCC GAG TAT GTC CCC AAA CCG TGC
Thr Leu Val His Leu MET Asn Pro Glu Tyr Val Pro Lys Pro Cys 1599            1608            1617            1626            1635
TGT GCG CCA ACT AAG CTA AAT GCC ATC TCG GTT CTT TAC TTT GAT
Cys Ala Pro Thr Lys Leu Asn Ala Ile Ser Val Leu Tyr Phe Asp 1644            1653            1662            1671            1680
GAC AAC TCC AAT GTC ATT CTG AAA AAA TAC AGG AAT ATG GTT GTA
Asp Asn Ser Asn Val Ile Leu Lys Lys Tyr Arg Asn MET Val Val 1689            1698            1708            1718            1728
AGA GCT TGT GGA TGC CAC TAACTCGAAA CCAGATGCTG GGGACACACA
Arg Ala Cys Gly Cys His
                (513)

1738            1748            1758            1768            1778
TTCTGCCTTG GATTCCTAGA TTACATCTGC CTTAAAAAAA CACGGAAGCA 1788            1798            1808            1818            1828
CAGTTGGAGG TGGGACGATG AGACTTTGAA ACTATCTCAT GCCAGTGCCT 1838            1848            1858            1868            1878
TATTACCCAG GAAGATTTTA AAGGACCTCA TTAATAATTT GCTCACTTGG 1888            1898            1908            1918            1928
TAAATGACGT GAGTAGTTGT TGGTCTGTAG CAAGCTGAGT TTGGATGTCT 1938            1948            1958            1968            1978
GTAGCATAAG GTCTGGTAAC TGCAGAAACA TAACCGTGAA GCTCTTCCTA 1988            1998            2008            2018            2028
CCCTCCTCCC CCAAAAACCC ACCAAAATTA GTTTTAGCTG TAGATCAAGC 2038            2048            2058            2068            2078
TATTTGGGGT GTTTGTTAGT AAATAGGGAA AATAATCTCA AAGGAGTTAA 2088            2098            2108            2118            2128
ATGTATTCTT GGCTAAAGGA TCAGCTGGTT CAGTACTGTC TATCAAAGGT 2138            2148            2158            2168            2178
AGATTTTACA GAGAACAGAA ATCGGGGAAG TGGGGGGAAC GCCTCTGTTC 2188            2198            2208            2218            2228
AGTTCATTCC CAGAAGTCCA CAGGACGCAC AGCCCAGGCC ACAGCCAGGG 2238            2248            2258            2268            2278
CTCCACGGGG CGCCCTTGTC TCAGTCATTG CTGTTGTATG TTCGTGCTGG
```

TABLE III-continued

```
          2288       2298       2308       2318       2328
    AGTTTTGTTG GTGTGAAAAT ACACTTATTT CAGCCAAAAC ATACCATTTC 2338       2348       2358       2368       2378
    TACACCTCAA TCCTCCATTT GCTGTACTCT TTGCTAGTAC CAAAAGTAGA 2388       2398       2408       2418       2428
    CTGATTACAC TGAGGTGAGG CTACAAGGGG TGTGTAACCG TGTAACACGT 2438       2448       2458       2468       2478
    GAAGGCAGTG CTCACCTCTT CTTTACCAGA ACGGTTCTTT GACCAGCACA 2488       2498       2508       2518       2528
    TTAACTTCTG GACTGCCGGC TCTAGTACCT TTTCAGTAAA GTGGTTCTCT 2538       2548       2558       2568       2578
    GCCTTTTTAC TATACAGCAT ACCACGCCAC AGGGTTAGAA CCAACGAAGA 2588       2598       2608       2618       2628
    AAATAAAATG AGGGTGCCCA GCTTATAAGA ATGGTGTTAG GGGGATGAGC 2638       2648       2658       2668       2678
    ATGCTGTTTA TGAACGGAAA TCATGATTTC CCTGTAGAAA GTGAGGCTCA 2688       2698       2708       2718       2728
    GATTAAATTT TAGAATATTT TCTAAATGTC TTTTTCACAA TCATGTGACT 2738       2748       2758       2768       2778
    GGGAAGGCAA TTTCATACTA AACTGATTAA ATAATACATT TATAATCTAC 2788       2798       2808       2818       2828
    AACTGTTTGC ACTTACAGCT TTTTTTGTAA ATATAAACTA TAATTTATTG 2838       2848       2858       2868       2878
    TCTATTTTAT ATCTGTTTTG CTGTGGCGTT GGGGGGGGGG CCGGGCTTTT 2888       2898       2908       2918
    GGGGGGGGGG GTTTGTTTGG GGGGTGTCGT GGTGTGGGCG GGCGG
```

Comparision of the sequence of murine Vgr-1 [Lyons, et al., PNAS 86:4554 (1989)] to human BMP-6 reveals a degree of amino acid sequence identity greater than 92% The murine Vgr-1 is likely the murine homologue of BMP-6. Human BMP-6 shares homology with other BMP molecules as well as other members of the TGF-β superfamily of molecules. The cysteine-rich carboxy-terminal 102 amino acid residues of human BMP-6 shares the following homologies with BMP proteins disclosed in copending applications described above: 61% identity with BMP-2; 44% identity with BMP-3, 60% identity with BMP-4; 91% identity with BMP-5; and 87% identity with BMP-7. Human BMP-6 further shares the following homologies: 41% identity with TGF-β3; 39% identity with TGF-β2; 37% identity with TGF-β1; 26% identity with Mullerian Inhibiting Substance (MIS), a testicular glycoprotein that causes regression of the Mullerian duct during development of the male embryo; 25% identity with inhibin α; 43% identity with inhibin $β_B$; 49% identity with inhibin $β_A$; 58% identity with Vgl, a Xenopus factor which may be involved in mesoderm induction in early embryogenesis (Weeks and Melton, Cell 51:861-867(1987)]; and 59% identity with Dpp the product of the Drosophila decapentaplegic locus which is required for dorsal-ventral specification in early embryogenesis and is involved in various other developmental processes at later stages of development [Padgett, et al., Nature 325:81-84 (1987)].

The procedures described above and additional methods known to those skilled in the art may be employed to isolate other related proteins of interest by utilizing the bovine or human proteins as a probe source. Such other proteins may find similar utility in, inter alia, fracture repair, wound healing and tissue repair.

Additional methods known to those skilled in the art may be used to isolate the genetic material encoding human and other species' cartilage/bone proteins of the invention.

EXAMPLE VI

Expression of the BMP-6 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention will be stably transformed mammalian cells. It is further contemplated that the preferred mammalian cells will be CHO cells. The transformed host cell is cultured and the BMP-6 proteins expressed thereby are recovered and purified. The recombinantly expressed BMP-6 proteins are free of proteinaceous materials with which they ordinarily are associated in nature and are purified from other proteinaceous materials with which they are co-produced as well as from other contaminants, such as materials found in the culture media.

In order to express biologically active human BMP-6 proteins, a selected host cell is transformed, using techniques known to those skilled in the art of genetic engineering, with a DNA sequence encoding human BMP-6 protein. The DNA encoding BMP-6 comprises nucleotide #1393 to #1698 set forth in Table III encoding amino acid #412 to #513. The transformed host cells are cultured and the BMP-6 protein comprising amino acid #412 to amino acid #513 as set forth in Table III is expressed. The expressed protein is recovered, isolated and purified form the culture and culture medium. The purified protein is substantally free from other proteinaceous materials with which it is co-produced as well as from other contaminants. In other embodiments, the DNA sequence utilized in expressing human BMP-6 proteins of the invention comprise the longer nucleotide sequence comprising nucleotide #1321 to #1698 encoding the amino acid sequence comprising #388 to #513. In further embodiment the DNA sequence utilized in expression comprises nucleotide #1303 to #1698 encoding the amino acid sequence comprising amino acid #382 to #513.

Expression in CHO cells for instance any comprise transformation of the host cell with a vector containing a DNA sequence comprising nucleotides #160 through #1712 of Table III. The transformed host cell is cultured and the expressed BMP-6 proteins are recovered and purified. It is contemplated that the recovered and purified BMP-6 protein comprises what is expected to be the mature form comprising amino acid #382-513. However, other forms of BMP-6 may be recovered and purified. These forms include proteins comprising amino acid #388-#513 and proteins comprising amino acid #412 to #513 as set forth in Table III.

One skilled in the art can construct mammalian expression vectors by employing the DNA sequences of the invention sequences and known vectors, such as pCD [Okayama et al., Mol. Cell Biol., 2:161-170 (1982)] and pJL3, pJL4 [Gough et al., EMBO J., 4:645-653 (1985)]. The transformation of these vectors into appropriate host cells may result in expression of the proteins of the invention.

One skilled in the art could manipulate the sequences of the invention by eliminating or replacing the mammalian regulatory sequences flanking the coding sequence with bacterial sequences to create bacterial vectors for intracellular or extracellular expression by bacterial cells. The coding sequences could be further manipulated, for example, ligated to other known linkers or modified by deleting non-coding sequences therefrom or altering nucleotides therein by other known techniques. The modified coding sequence could then be inserted into a known bacterial vector using procedures such as described in T. Taniguchi et al., Proc. Natl Acad. Sci. USA, 77:5230-5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601-629 (1982). This approach can be employed with a number of different cell types.

For example, a plasmid containing a DNA sequence for a protein of the invention in operative association with other plasmid sequences enabling expression thereof and the DHFR expression plasmid pAdA26SV-(A)3 [Kaufman and Sharp, Mol. Cell. Biol., 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., Mol Cell Biol., 5:1750 (1983). Protein expression should increase with increasing levels of MTX resistance.

Transformants are cloned, and the proteins of the invention are recovered, isolated, and purified from the culture medium. Biologically active protein expression is monitored by the Rosen-modified Sampath-Reddi rat bone formation assay described above in Example III. Similar procedures can be followed to produce other related proteins.

EXAMPLE VII

Biological Activity of Expressed BMP-6 Proteins

To measure the biological activity of the expressed proteins obtained in Example VI above, the BMP-6 proteins are recovered from the culture media and purified. BMP-6 may be partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15M NaCl, pH 7.4 (starting buffer). This material is then applied to a 1.1 ml Heparin Sepharose column in starting buffer. Unbound proteins are removed by an 8 ml wash of starting buffer, and bound proteins, including proteins of the invention, are desorbed by a 3-4 ml wash of 20 mM Tris, 2.0M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-6 proteins of the invention have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Levels of activity may also be tested for host cell extracts. Partial purification is accomplished in a similar manner as described above except that 6 M urea is included in all the buffers.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA sequence encoding a BMP-6 protein said DNA sequence comprising the nucleotide sequence selected from the group consisting of:
   a) nucleotide #1 through nucleotide #666 of FIG. 2;
   b) nucleotide #1393 to #1698 of FIG. 3;
   c) nucleotide #1 to #2393 of FIG. 3;
   d) nucleotide #160 to #1698 of FIG. 3;
   e) nucleotide #1303 to #1698 FIG. 3;
   f) allelic variants and degenerative sequences of (a) through (d); and g) sequences which
      (1) hybridize to said DNA sequence under stringent hybridization conditions; and
      (2) encode a protein characterized by the ability to induce the formation of cartilage and/or bone in the Rose-modified Sampath-Reddi assay.

2. A vector comprising a DNA sequence of claim 1 in operative association with an expression control sequence therefor.

3. A host cell transformed with a vector of claim 2.

4. A host cell of claim 3 wherein said host cell is a mammalian cell.

5. An isolated DNA sequence encoding the BMP-6 protein of FIG. 3 or a fragment thereof which encodes a protein characterized by the ability to induce the formation of cartilage and/or bone in the Rosen-modified Sampath-Reddi assay" after "3".

6. An isolated DNA sequence encoding a BMP-6 protein said sequence comprising nucleotide #1 to #2923 of FIG. 3.

7. A vector comprising the nucleotide sequence of claim 6.

8. A host cell transformed with the vector of claim 7.

9. The host cell of claim 8 wherein said host cell is a mammalian cell.

10. A method for producing a purified BMP-6 protein said method comprising the steps of
    (a) culturing in a suitable culture medium cells transformed with a DNA sequence comprising the DNA nucleotide #1 to #2923 of FIG. 3; and
    (b) isolating and purifying said protein from said culture medium said BMP-6 protein.

11. An isolated DNA sequence encoding a BMP-6 protein said sequence comprising nucleotide #160 to #1698 of FIG. 3.

12. A vector comprising the nucleotide sequence of claim 11.

13. A host cell transformed with the vector of claim 12.

14. The host cell of claim 13 wherein said host cell is a mammalian cell.

15. A method for producing a purified BMP-6 protein said method comprising the steps of
    (a) culturing in a suitable culture medium cells transformed with a DNA sequence comprising the DNA nucleotide #§to #1698 of FIG. 3; and
    (b) isolating and purifying said protein from said culture medium said BMP-6 protein.

16. An isolated DNA sequence encoding a BMP-6 protein said sequence comprising nucleotide #1303 to #1698 of FIG. 3.

17. A vector comprising the nucleotide sequence of claim 16.

18. A host cell transformed with the vector of claim 17.

19. The host cell of claim 18 wherein said host cell is a mammalian cell.

20. A method for producing a purified BMP-6 protein said method comprising the steps of
    (a) culturing in a suitable culture medium cells transformed with a DNA sequence comprising the DNA nucleotide #1303 to #1698 of FIG. 3; and
    (b) isolating and purifying said protein from said culture medium said BMP-6 protein.

21. An isolated DNA sequence encoding a BMP-6 protein said sequence comprising nucleotide #1393 to #1698 of FIG. 3.

22. A vector comprising the nucleotide sequence of claim 21.

23. A host cell transformed with the vector of claim 22.

24. The host cell of claim 23 wherein said host cell is a mammalian cell.

25. A method for producing a purified BMP-6 protein said method comprising the steps of
    (a) culturing in a suitable culture medium cells transformed with a DNA sequence comprising the DNA nucleotide #1393 to #1698 of FIG. 3; and
    (b) isolating and purifying said protein form said culture medium said protein comprising amino acid #412 to #513 as shown in FIG. 3.

26. An isolated DNA sequence encoding the BMP-6 protein of FIG. 2.

27. An isolated DNA sequence encoding a BMP-6 protein comprising the nucleotide sequence from nucleotide #1 to #666 of FIG. 2.

* * * * *